(12) United States Patent
Kirn

(10) Patent No.: US 10,045,808 B2
(45) Date of Patent: Aug. 14, 2018

(54) DEVICE FOR EFFECTING CHANGE IN TISSUE AT A TREATMENT SITE

(71) Applicant: KIRN MEDICAL DESIGN LLC, Lexington, KY (US)

(72) Inventor: David S. Kirn, Lexington, KY (US)

(73) Assignee: KIRN MEDICAL DESIGN, LLC, Lexington, KY (US)

( * ) Notice: Subject to any disclaimer, the term of this patent is extended or adjusted under 35 U.S.C. 154(b) by 806 days.

(21) Appl. No.: 14/559,240

(22) Filed: Dec. 3, 2014

(65) Prior Publication Data

US 2015/0150619 A1 Jun. 4, 2015

Related U.S. Application Data

(60) Provisional application No. 61/911,131, filed on Dec. 3, 2013.

(51) Int. Cl.
*A61B 18/02* (2006.01)
*A61B 18/00* (2006.01)

(52) U.S. Cl.
CPC .... *A61B 18/02* (2013.01); *A61B 2018/00452* (2013.01); *A61B 2018/00577* (2013.01); *A61B 2018/00714* (2013.01); *A61B 2018/00791* (2013.01); *A61B 2018/0243* (2013.01); *A61B 2018/0256* (2013.01)

(58) Field of Classification Search
CPC ....................... A61B 18/02; A61B 2018/00452
USPC ......................................................... 606/23
See application file for complete search history.

(56) References Cited

U.S. PATENT DOCUMENTS

| | | |
|---|---|---|
| 5,830,208 A | 11/1998 | Muller |
| 6,017,337 A | 1/2000 | Pira |
| 6,104,959 A | 8/2000 | Spertell |
| 6,120,497 A | 9/2000 | Anderson et al. |
| 6,264,649 B1 | 7/2001 | Whitcroft et al. |
| 6,273,885 B1 | 8/2001 | Koop et al. |
| 6,632,219 B1 | 10/2003 | Baranov et al. |
| 6,659,999 B1 | 12/2003 | Anderson et al. |
| 6,743,222 B2 | 6/2004 | Durkin et al. |
| 7,006,874 B2 * | 2/2006 | Knowlton .............. A45D 44/22 607/101 |
| 7,041,094 B2 | 5/2006 | Connors et al. |
| 7,077,840 B2 | 7/2006 | Altshuler et al. |
| 7,189,230 B2 | 3/2007 | Knowlton |
| 7,204,832 B2 | 4/2007 | Altshuler et al. |
| 2007/0038206 A1 * | 2/2007 | Altshuler ............. A61B 18/203 606/20 |

\* cited by examiner

*Primary Examiner* — Nadia A Mahmood
(74) *Attorney, Agent, or Firm* — Michael S. Hargis; King & Schickli, PLLC

(57) ABSTRACT

A device for effecting change in tissue at a treatment site includes a housing having an aperture for receiving a user's finger, a cold plate supported by said housing for cooling the tissue at the treatment site, and at least one thermoelectric cooling semiconductor thermally coupled to said cold plate and electrically coupled to a power source. In another embodiment, the cold plate may include a surface for contacting the treatment site, and at least a portion of said cold plate including said surface may extend from said housing.

37 Claims, 11 Drawing Sheets

DEVICE FOR EFFECTING CHANGE IN TISSUE AT A TREATMENT SITE

This application claims the benefit of U.S. Provisional Patent Application No. 61/911,131, filed Dec. 3, 2013, the disclosure of which is incorporated herein by reference.

TECHNICAL FIELD

The present invention relates generally to the field of skin treatment; and more particularly to a device for effecting change in tissue at a treatment site.

BACKGROUND OF THE INVENTION

Many different devices and methods have been used for skin treatments intended to improve the texture and appearance of the skin. All share a common mechanism, i.e., they selectively destroy a portion of the skin allowing the body to heal with fresh, new, and hopefully undamaged skin cells. Recovery time from such procedures is in direct correlation to the depth of skin destruction.

Existing devices and methods also share another common feature, i.e., none of them provide a method of monitoring the depth of treatment while the destruction is actually occurring. Rather, the clinician must follow a protocol and visibly observe changes in the skin to yield treatment which is deep enough to be effective, but not too deep to cause scarring, pigmentation changes, or prolonged healing. The difficulty of achieving accuracy in treatment is compounded, for example, by changes in skin thickness and blood flow from one body area to another as well as patient to patient differences in skin type, pigmentation, degree of sun damage, and general health of the skin.

More specifically, cyrosurgery with liquid nitrogen has been used for decades to freeze off skin lesions, such as warts and other non-malignant growths. Application of the liquid nitrogen causes a coagulative necrosis of whatever viable tissue it contacts. The key advantage of cryosurgery over other ablative techniques is the fact that cold temperatures are much better tolerated by the patient than hot temperatures. A laser or thermal cautery would be equally effective for removal of skin lesions, but these methods are painful and poorly tolerated by the patient in the absence of an anesthetic. The disadvantages of cryosurgery, on the other hand, include a lack of precise control of the zone of tissue ablation and difficulty achieving limited zones of tissue ablation due to the extremely low temperature of liquid nitrogen relative to body temperature. It is also difficult to achieve any change in the tissue other than ablation due to the extremely low temperatures associated with liquid nitrogen. This essentially precludes any tissue treatment other than ablation.

Others have attempted to overcome the disadvantages associated with laser or thermal cautery devices by using cryogen spray to cool the treatment area during the procedure which results in a more tolerable, but temporary, anesthesia effect. Despite the improvement, none of these devices provide real-time monitoring of the skin while the cooling process is taking effect to ensure that the skin has been cooled sufficiently to provide the desired anesthetic effect. Even more, none of the noted devices are designed for convenient and simple operation by a user or for monitoring of the temperature near the treatment site by the user.

Accordingly, a need exists for a device and related method for effecting change in tissue at a treatment site which monitors the temperature at the treatment site in order to provide real time feedback during treatment. The device would also control the temperature of the tissue at the treatment site dependent upon the sensed temperature in order to effect changes other than simple ablation. The device would be easy to use and provide features designed to limit patient risk. The device could also be designed to be operated by the user with a single hand. Even more, the device could be designed to be positioned on one or more fingers of the user allowing adjacent fingers to stabilize the device during use and monitor the temperature of the skin surrounding the treatment area. All of these features are provided by the following invention. Naturally, any improvements along such lines should contemplate good engineering practices, such as simplicity, ease of implementation, unobtrusiveness, stability, etc.

SUMMARY OF THE INVENTION

The present invention meets these needs by providing a device for effecting change in tissue at a treatment site. In one embodiment, the device for effecting change in tissue at a treatment site includes a housing having an aperture for receiving a user's finger, a cold plate supported by the housing for cooling the tissue at the treatment site, and at least one thermoelectric cooling semiconductor thermally coupled to the cold plate and electrically coupled to a power source. In another embodiment, the cold plate may include a surface for contacting the treatment site, and at least a portion of the cold plate including the surface may extend from the housing.

In another embodiment, the aperture for receiving the user's finger is a longitudinal bore, and the housing includes at least one exterior surface for contacting a second finger of the user to stabilize the device during use. In yet another, the housing includes a first surface for contacting a second finger of the user and a second surface for contacting a third finger of the user. In this embodiment, the first and second surfaces are juxtaposed to the aperture for receiving the user's finger. In yet another embodiment, the first and second surfaces are on opposing sides of the aperture for receiving the user's finger. In still another embodiment, the aperture is a longitudinal bore and the first and second surfaces form open channels.

In a different embodiment, a sheath is connected to the device adjacent the cold plate to prevent contact between the device and the treatment site.

In yet another embodiment, the device may also include a heat sink thermally coupled to the at least one thermoelectric cooling semiconductor, a sensor for sensing a temperature at the treatment site, and a controller electrically coupled to the power source, the controller for controlling the temperature of the treatment site dependent upon the sensed temperature of the treatment site and a target temperature. In another embodiment, the temperature of the treatment site is a temperature of the cold plate. In this embodiment, the cold plate includes a surface for contacting the treatment site, and at least a portion of the cold plate including the surface extends from the housing.

In another embodiment, a device for effecting change in tissue at a treatment site includes a power source, a cold plate for cooling the tissue at the treatment site, at least one thermoelectric cooling semiconductor thermally coupled to the cold plate and electrically coupled to the power source, a heat sink thermally coupled to the at least one thermoelectric cooling semiconductor, a sensor for sensing a temperature at the treatment site, and a controller electrically coupled to the power source, the controller for controlling the temperature of the treatment site dependent upon the sensed temperature of the treatment site. In one embodiment, the sensor is an infrared thermometer. In another, the temperature of the treatment site is a temperature of the cold plate.

In yet another embodiment, the change in the tissue is a tissue function change and the temperature sufficient to effect the tissue function change at the treatment site is maintained by the controller at approximately −1° C. In this embodiment, the cold plate includes a surface for contacting the treatment site, and at least a portion of the cold plate including the surface extends from a housing supporting the cold plate. In a related embodiment, the device may further include a housing having an aperture for receiving a user's finger. The aperture for receiving the user's finger may be a longitudinal bore, and the housing may include at least one exterior surface for contacting a second finger of the user to stabilize the device during use.

In another embodiment, the change in the tissue is ablation of the tissue and the temperature sufficient to ablate the tissue at the treatment site is maintained by the controller at or below approximately −40° C. In this embodiment, the device may include a housing having an aperture for receiving a user's finger. Moreover, the aperture for receiving the user's finger may be a longitudinal bore, and the housing may include at least one exterior surface for contacting a second finger of the user to stabilize the device during use.

In still another embodiment, a method of effecting change in tissue at a treatment site comprises the steps of positioning a cold plate in thermal contact with tissue at the treatment site, cooling the cold plate to a temperature sufficient to effect change in the tissue at the treatment site, sensing a temperature at the treatment site and generating a signal indicative of the temperature, and controlling the cooling of the cold plate dependent upon the sensed temperature.

In another embodiment, the controlling step includes maintaining the temperature sufficient to effect change in the tissue at the treatment site between approximately −1° C. and −40° C. In yet another, the cooling step includes energizing at least one thermoelectric cooling semiconductor thermally coupled to the cold plate for cooling the cold plate to a predetermined temperature sufficient to effect change in the tissue at the treatment site.

In still another embodiment, the step of maintaining the temperature sufficient to effect change in the tissue at the treatment site is repeated for a predetermined period of time, and the step of cooling may be ended at the end of the predetermined period of time. In another embodiment, the controlling step includes maintaining the temperature sufficient to effect change in the tissue at the treatment site for a period of time.

In another embodiment, the positioning step includes inserting at least one finger into an aperture of a housing supporting the cold plate.

In yet another, the method may include the step of stabilizing the cold plate in thermal contact with tissue at the treatment site. In another embodiment, the stabilizing step includes inserting at least one finger into an aperture of a housing supporting the cold plate.

In a further embodiment, a method of effecting change in tissue at a treatment site comprises the steps of positioning a cold plate in thermal contact with tissue at the treatment site, energizing at least one thermoelectric cooling semiconductor thermally coupled to the cold plate for gradually cooling the cold plate to a predetermined temperature sufficient to effect change in the tissue at the treatment site, sensing a temperature at the treatment site, and adjusting the energy applied to the at least one thermoelectric cooling semiconductor in order to maintain the temperature at the treatment site at a desired.

In another embodiment, the method may include the step of removing the energy applied to the at least one thermoelectric cooling semiconductor at the end of the period of time. In still another, the step of adjusting the energy applied to the at least one thermoelectric cooling semiconductor is repeated for a predetermined period of time, and the method may include the step of ending the energizing at the end of the predetermined period of time. In another embodiment, the adjusting step depends upon the sensed temperature at the treatment site. Other related embodiments, may include the step of inserting at least one finger into an aperture of a housing supporting the cold plate. Still others may include the step of stabilizing the cold plate in thermal contact with tissue at the treatment site. In another embodiment, the stabilizing step includes inserting at least one finger into an aperture of a housing supporting the cold plate.

Additional advantages and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

BRIEF DESCRIPTION OF THE DRAWINGS

The accompanying drawings incorporated in and forming a part of the specification, illustrate several aspects of the present invention, and together with the description serve to explain the principles of the invention. In the drawings.

Reference will now be made in detail to the present preferred embodiment of the invention, an example of which is illustrated in the accompanying drawings.

DETAILED DESCRIPTION OF THE PREFERRED EMBODIMENT

Figure 1:
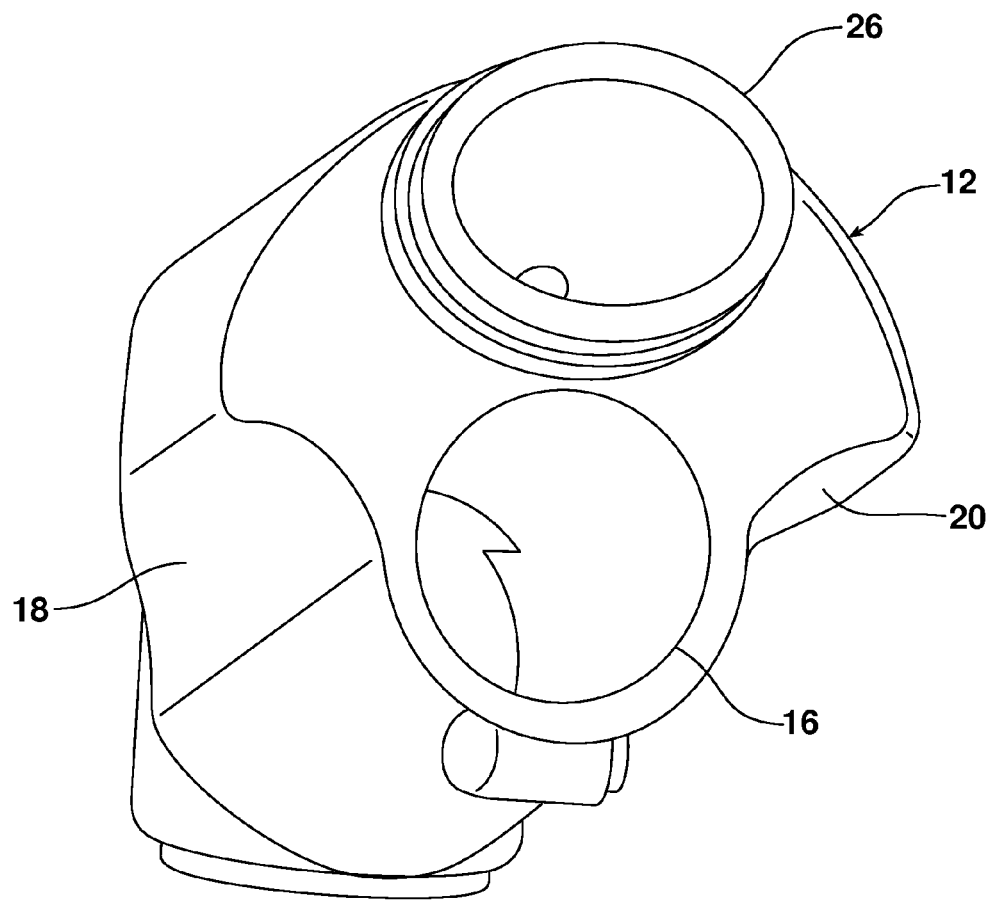
FIG. 1 is a plan view of a housing of a skin treatment device positioned on a user's finger.

With reference to FIG. 1, there is shown a housing 12 of a device 10 intended for effecting change in tissue at a treatment site by cooling the tissue at the treatment site. As described in more detail below, the device 10 also includes a base unit 14 that is connected to the housing 12 during operation.

In the present embodiment, the housing 12 includes an aperture 16 for receiving a user's finger. The aperture 16 is a longitudinal bore within which the user's finger is positioned during use to support the housing 12. The longitudinal bore 16 could be wider in different embodiments for receiving more than one of the user's fingers. The present housing 12 also includes two exterior surfaces 18, 20 for contacting second and third fingers of the user to stabilize the housing 12 during use. As shown, the exterior surfaces 18, 20 of the housing 12 are juxtaposed to the aperture 16. More specifically, in this embodiment, the exterior surfaces 18, 20 are on opposing sides of the aperture 16 and form open channels for receiving the user's second and third fingers.

Figure 2:
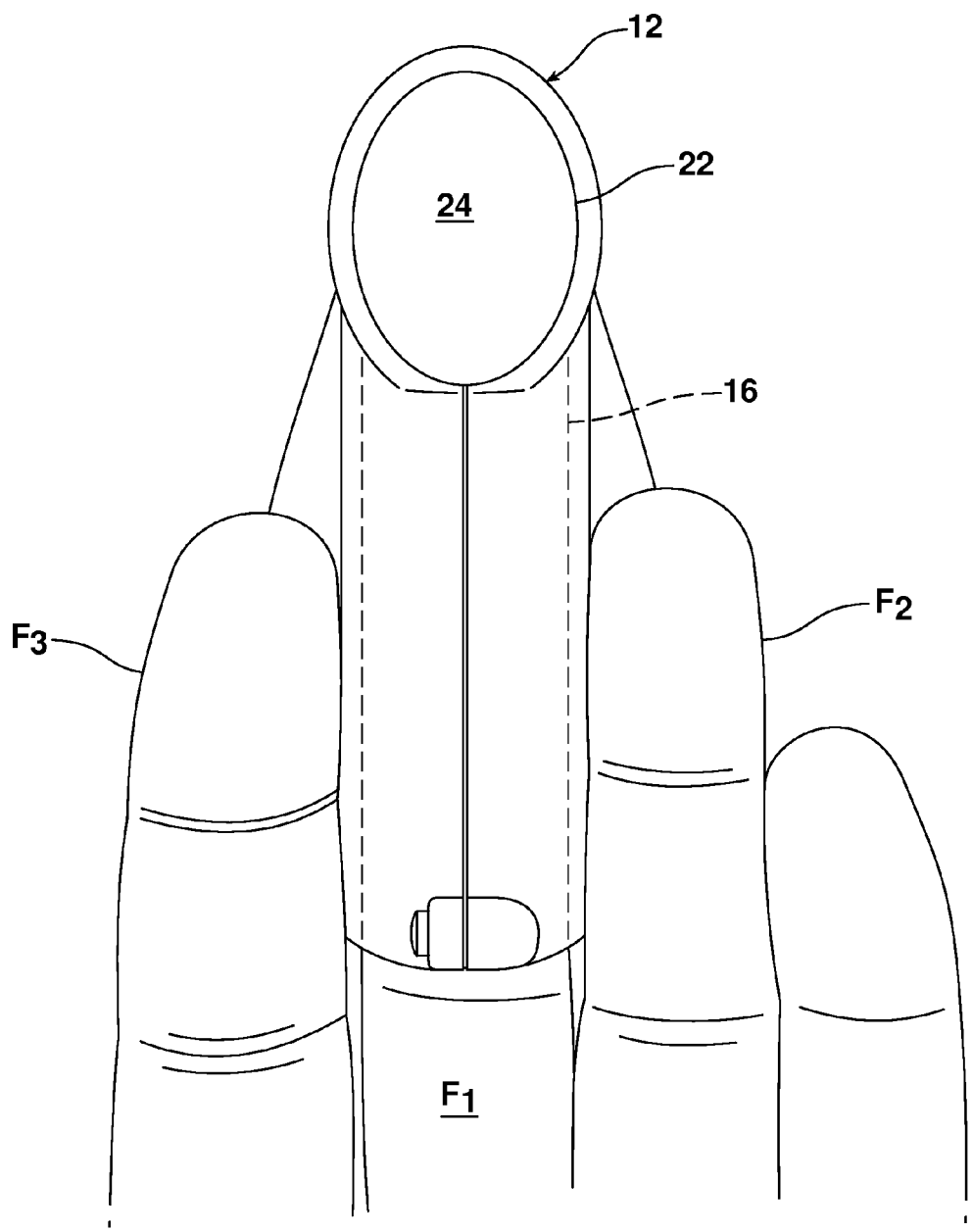
FIG. 2 is a perspective view of a housing illustrating an aperture for receiving the user's finger and external surfaces used to provide stability during use.

As shown in FIG. 2, the user's finger ($F_1$) is inserted into the longitudinal bore 16 of housing 12. As shown, the user's palm (P) is facing upwards and the second and third fingers ($F_2$, $F_3$) are juxtaposed to the longitudinal bore 16 and positioned on opposing sides of the housing 12. Upper and side surfaces of the second and third fingers are in contact with the exterior surfaces 18, 20 of the housing 12. In other words, the second and third fingers are positioned within the open channels formed by the exterior surfaces 18, 20 on opposing sides of the longitudinal bore 16. In this manner, the user can support the housing 12 with the finger $F_1$ and provide stabilization during use with the fingers $F_2$ and $F_3$.

More specifically, the user can apply a downward force to the housing 12 using finger $F_1$ and at the same time apply upward or stabilizing forces using fingers $F_2$ and $F_3$ This provides the user with a certain level of control and stability of the housing 12. Although not shown, an elastic band or spring loaded clip may be added to secure the housing 12 on the user's finger $F_1$. In some applications, it is useful for the user to apply and maintain pressure on a treatment area. The exterior surfaces 18, 20 on opposing sides of the longitudinal bore 16 also allow the user's fingers $F_2$ and $F_3$ to contact the patient's skin adjacent the treatment area. This provides a reference point for further stabilization using the fingers $F_2$ and $F_3$ and allows the user to sense the temperature adjacent the treatment site in addition to any mechanically sensed feedback.

As further shown in FIG. 2, a cold plate 22 is supported by the housing 12. The cold plate 22 is positioned at a distal end of the housing 12 and includes a generally oval-shaped surface 24 in the present embodiment. This shape generally coincides with the digital pulp of finger $F_1$ and is sufficiently compact to allow the surface 24 of cold plate 22 to reach into tight treatment areas such as on and around a patient's face. Of course, the surface 24 of the cold plate 22 can be any shape in accordance with the present invention. The cold plate 22 may be made of copper, ceramic, or other material of high thermal conductivity, and a thermal mass of the cold plate is kept to a minimum in the present embodiment to allow for rapid temperature change.

Figure 3:
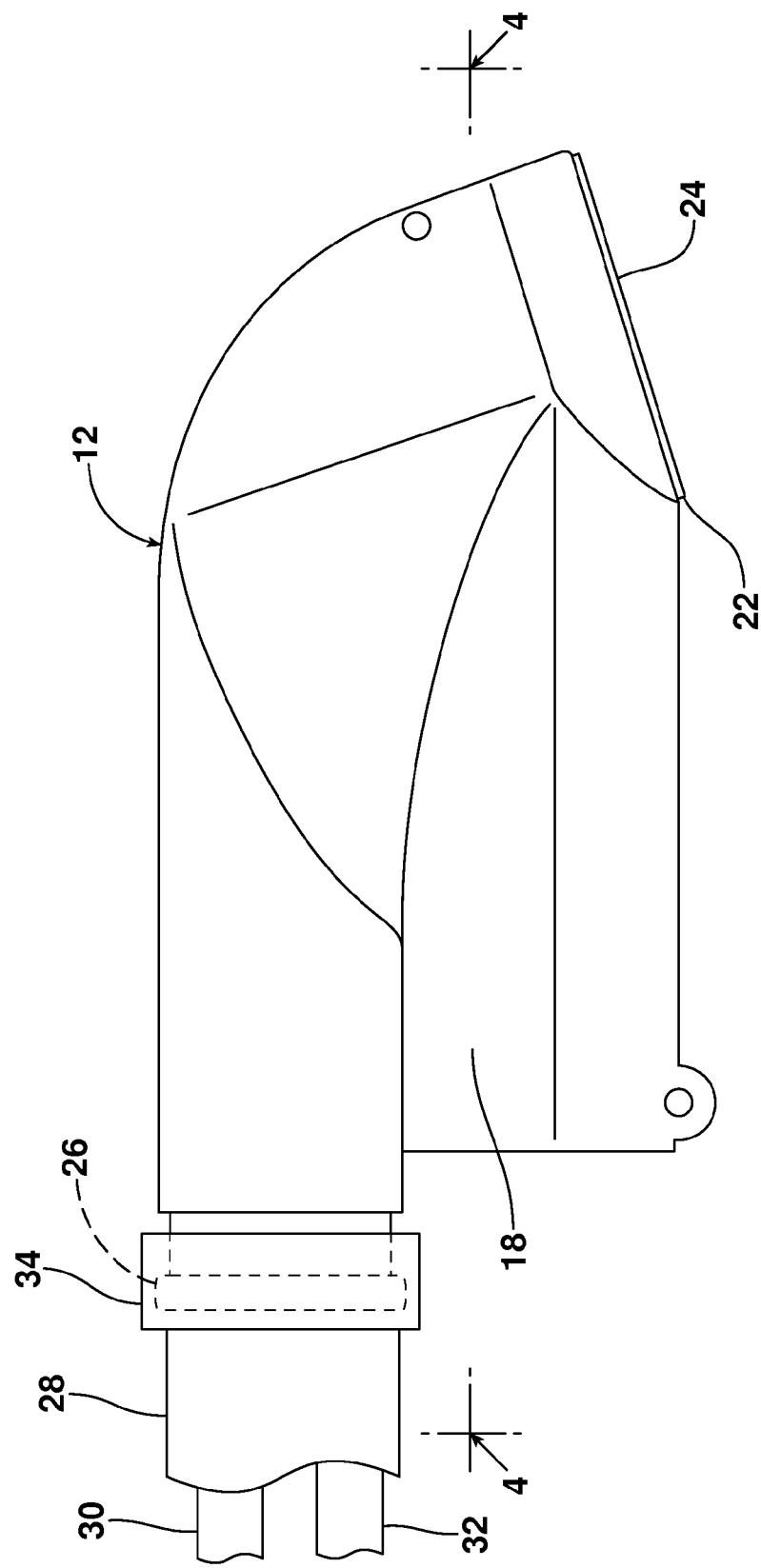
FIG. 3 is a side elevational view of the housing of the skin treatment device.

As shown in FIG. 3, surface 24 of cold plate 22 faces away from housing 12. More specifically, a portion of the cold plate 22 including the surface 24 extends from the housing 22 for contacting the treatment site. In one embodiment, a disposable sheath (not shown) is used in order to maintain cleanliness of the housing 12. As will be described in more detail below with regard to an alternate embodiment, a recess may be provided for attachment of the disposable sheath (see FIGS. 11, 12A, and 12B). The sheath is supported by the housing to prevent contact between the cold plate/housing and the treatment site. In yet another embodiment, a thermally conductive medium, such as a liquid or gel, could be used between the sheath and the treatment site.

A fitting 26 (shown in dashed lines) is provided for connecting the housing 12 to the base unit 14 during operation. More specifically, a cable 28 including fluid, power and signal lines covered in a plastic or rubber outer layer connects corresponding lines within the housing 12 and the base unit 14. In the present embodiment, the cable 28 includes a fluid line 30 and an electrical line 32 within a flexible outer layer and its length may vary. Cable fitting 34 couples with the housing fitting 26 and a similar base unit fitting 36. Although single fittings integrate the fluid line 30 and the electrical line 32 in the present embodiment, multiple housing and base unit fittings may be utilized to accommodate multiple cables. Other embodiments may utilize wireless communication technology between the housing and the base unit including, for example, infra red or Wi-Fi technology.

In the present embodiment, the fitting 26 is positioned adjacent the longitudinal bore 16 such that cable 28 extends from the housing 12 in the general direction formed by the longitudinal bore 16 and the user's finger $F_1$. Positioning of the fitting 26 above the longitudinal bore 16 allows the cable 28 to traverse the back of the user's hand which is away from the treatment site.

Figure 4:
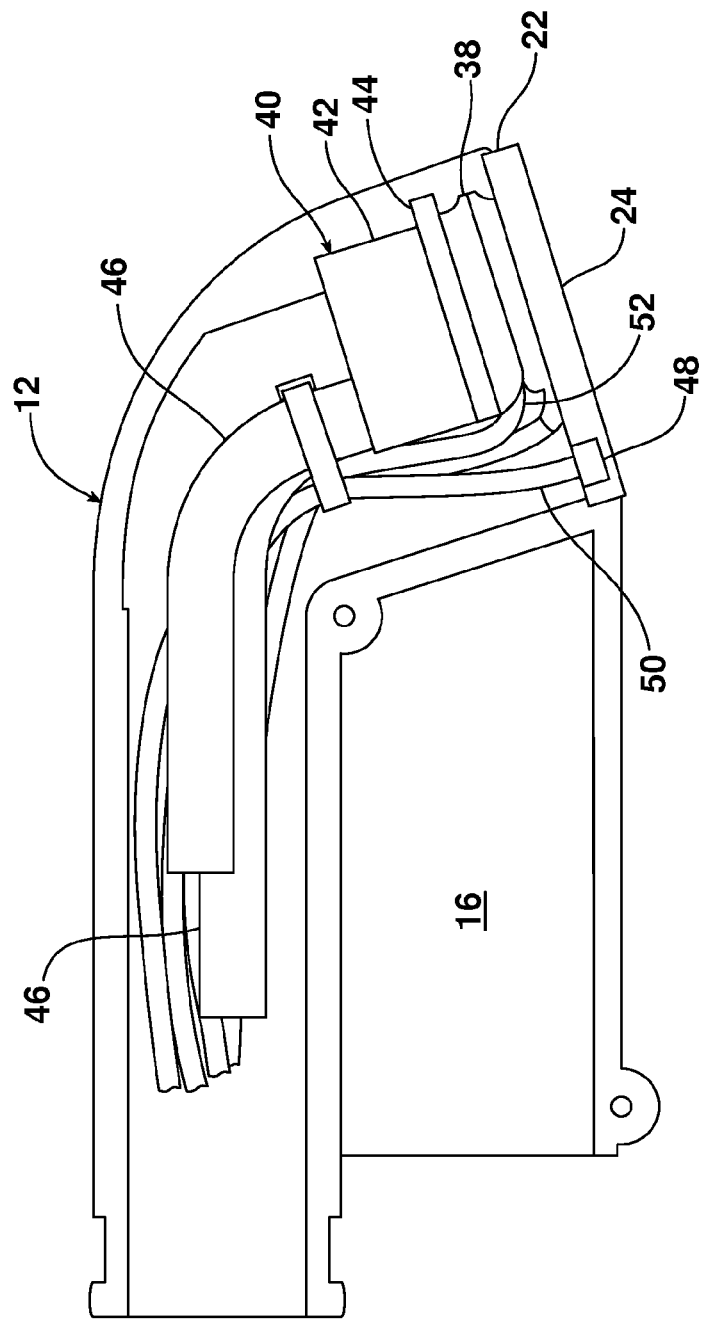
FIG. 4 is a section view of FIG. 3 showing a cold plate and TEC stack within the housing.

As shown in FIG. 4, the cold plate 22 is thermally coupled to a thermoelectric cooling semiconductor 38 within the housing 22. Thermal coupling supports thermal transfer between parts and can be accomplished in many ways known in the art. For example, the parts could be directly coupled or a thermal epoxy or other medium could be used. In the present embodiment, the thermoelectric cooling semiconductor 38 is a stacked array of thermoelectric cooling semiconductors or an TEC stack. In alternate embodiments, the TEC stack could include larger and/or additional thermoelectric cooling semiconductors which would provide a lower temperature at the treatment site. Such alternatives are dependent in some embodiments on the size of the housing. The TEC stack 38 is also electrically coupled to a power source 40 through electrical line 32 of cable 28. The power source 40 is positioned within base unit 14 in the present embodiment. In alternate embodiments, the power source could be positioned within the housing.

The TEC stack 38 is also thermally coupled to a heat sink 40. The heat sink 40 in the present embodiment is a water block having an upper portion 42 and a lower portion 44. Other types of heat sinks may be used in this and alternate embodiments to dissipate heat as is know in the art. The lower portion 44 of water block 40 is thermally coupled to the TEC stack 38 to support thermal transfer, i.e., to remove heat generated by operation of the TEC stack. Specifically, fluid is circulated to the water block 40 to transfer heat away from a hot side of TEC stack 38. Altogether, the cold plate 22, TEC stack 38, and water block 40 are held together in the present embodiment using a mechanical fastener (e.g., a screw) which is not shown.

In the present embodiment, the fluid is pumped from the base unit 14 through the fluid line 30 to housing 12. Rigid fluid tubing 46 connects the water block 40 and the fluid line 30. The fluid line 30 includes a first line for cooled fluid pumped from the base unit 14 and a second line for returning fluid warmed by the TEC stack 38 back to the base unit. In the present embodiment, the fluid line 30 is flexible and routed within cable 28 away from the treatment site. Further description of the base unit 2 and fluid circulation is provided below.

The device for effecting change in tissue at a treatment site of the present embodiment also includes a sensor 48 for sensing a temperature at the treatment site. The present sensor 48 generates a signal ($S_{Temp}$) indicative of a sensed temperature at the treatment site throughout operation of the device. The temperature of the cold plate 22 is synonymous with the temperature at the treatment site. In alternate embodiments, the sensor may be an infrared thermometer for measuring a temperature of the tissue at the treatment site. A window (not shown) may be positioned adjacent the treatment site through which the infrared thermometer visualizes the tissue. The window may be made of Germanium due to its favorable infrared characteristics, Germanium oxides, or similar materials having such characteristics in other embodiments.

As shown in FIG. 4, the sensor 48 is embedded in the cold plate 22. Alternatively, the sensor 48 may be located adjacent to and in contact with the cold plate 22, or positioned between the cold plate and the TEC stack. Wires 50 connecting the sensor 48 to the controller 54 and wires 52 connecting the TEC stack 38 to the power source 40 form the electrical line 32 of cable 28. The signal ($S_{Temp}$) generated by the sensor 48 is transmitted to a controller 54 for controlling the temperature of the treatment site. The controller 54, which is a microprocessor in the present embodiment, in turn controls the TEC stack 38 dependent upon the sensed temperature and a target temperature.

In other words, the sensor 48 senses a temperature at the treatment site (either of the cold plate or the patient's skin at the treatment site), and provides a signal indicative of that temperature. The sensed temperature is then compared within the controller 54 to a desired or predetermined treatment site temperature. Depending upon the outcome of that comparison, the TEC stack 38 is controlled by controller 54 to either raise or lower the temperature at the treatment site. This real time feedback loop continues throughout the process for effecting change in tissue.

In the present embodiment, the temperature sufficient to effect change in the tissue at the treatment site is maintained by the controller 54. When the change in tissue is a tissue function change, for example, the temperature sufficient to effect the tissue function change at the treatment site may be maintained by the controller 54 at approximately −1° C. When the change in tissue is ablation of the tissue, for example, the temperature sufficient to ablate the tissue at the treatment site may be maintained by the controller 54 at or below approximately −40° C. In operation, the operator may control the temperature to any degree desired but the approximately −1° C. temperature has been determined to be sufficient to effect tissue function change in most instances at the treatment site and the approximately −40° C. temperature has been determined to be sufficient to ablate tissue at the treatment site. Of course, these approximated temperatures may vary from patient to patient, and procedure to procedure depending upon many factors including, for example, the type of tissue function change desired, location of the tissue and other factors that affect treatment as described herein.

Figure 5:
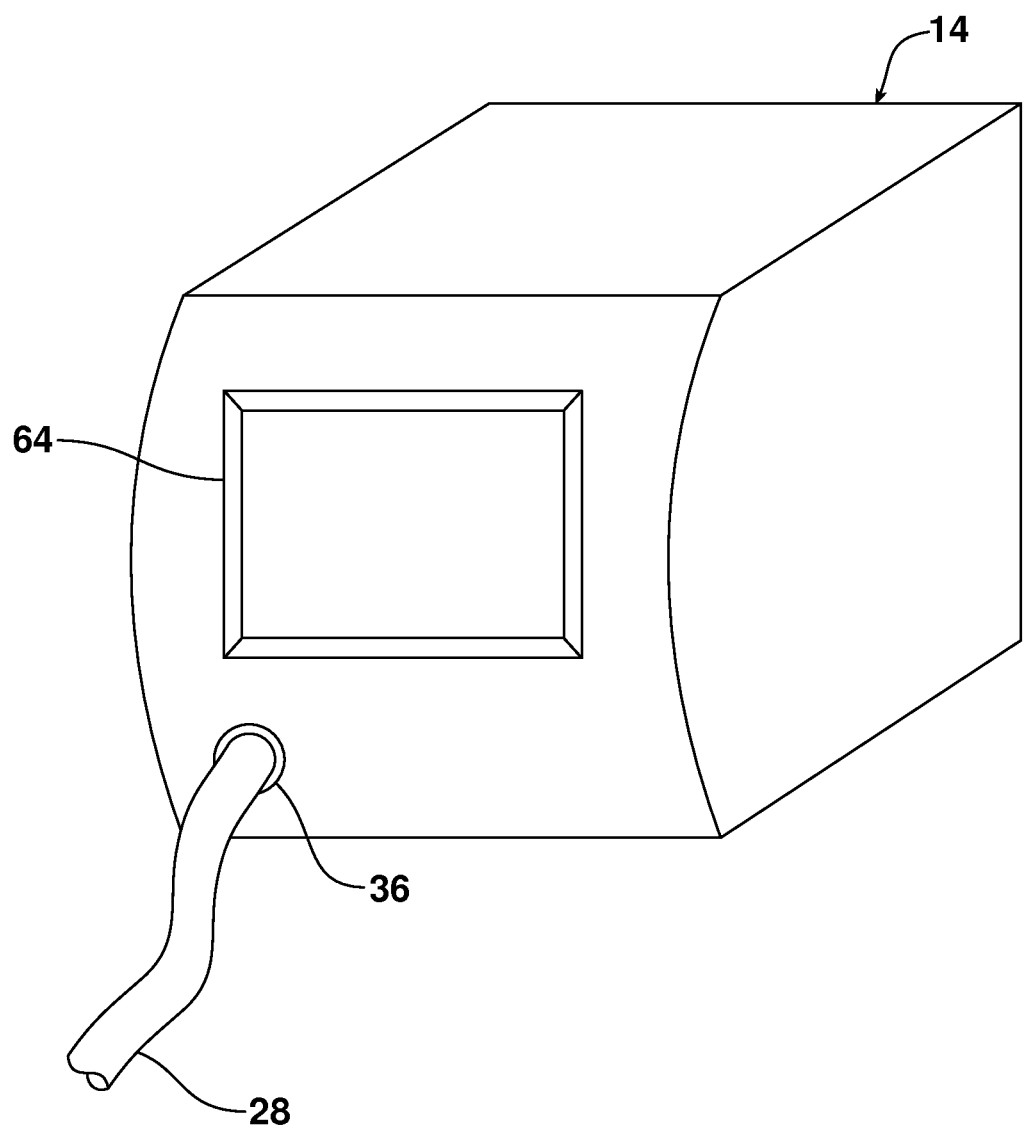
FIG. 5 is a perspective view of a base unit and a touch screen display.
Figure 6:
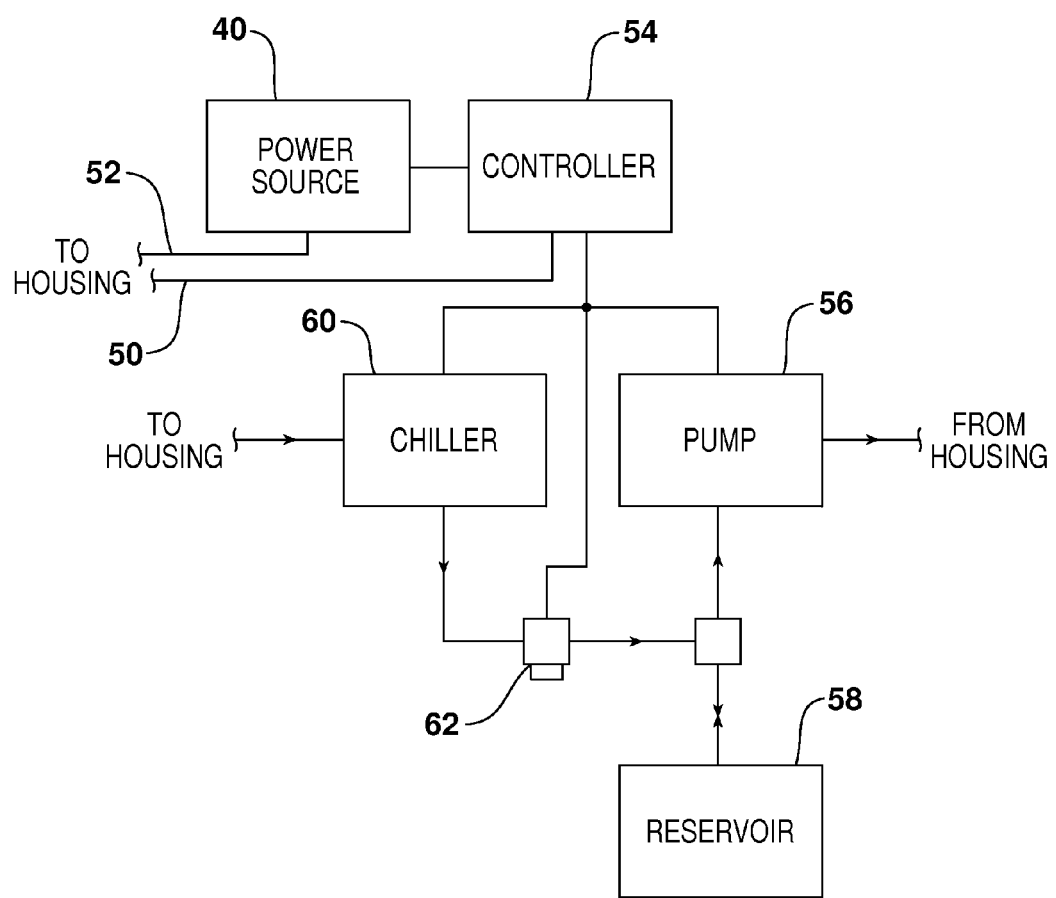
FIG. 6 is a schematic of the base unit.

As shown in FIG. 5, the base unit 14 is connected to the housing 12 by cable 28 via fitting 36. In alternate embodiments, the base unit may take any form and the base unit and housing could be combined into a unitary hand-held device. As shown in the schematic of FIG. 6, the base unit 14 in the present embodiment includes a power source 40, a controller 54, a pump 56, a fluid reservoir 58, and a chiller 60. As indicated above, the cable 28 includes a fluid line 30 to form a closed loop circulation system.

The present circulation system includes the pump 56, the fluid line 30, the housing 12, the chiller 60, a thermocouple 62, and connecting fluid lines (designated in FIG. 6 by lines with arrows thereon). The fluid reservoir 58 serves as an expansion tank but is not a direct part of fluid flow in the present circulation system. In a more minimalistic embodiment, the chiller 60 may be removed from the system. Due to the significant amount of heat typically generated by an TEC stack, however, the chiller 60 is incorporated in the present embodiment. More specifically, the chiller 60 is a modular unit which incorporates at least one additional thermoelectric cooling semiconductor, or TEC stack, and an air cooled heat sink/radiator with or without a fan. A fluid temperature within the circulation system is regulated by a thermocouple 62 electrically connected to controller 54 and is maintained by the controller and chiller 60 at a constant set point throughout operation.

The base unit 12 of the present embodiment also includes a display 64, such as a touch screen display, user interface, or other alternative means of control for user input. In the present embodiment, the display 64 is a touch screen display that allows users to select operational parameters and settings. Alternate embodiments may include a display on one or both of the housing or the base unit. Preset cycles included desired treatment site temperatures and application time periods, for example, may be pre-configured but the present embodiment allows the user to modify all parameters and settings independently.

Figure 7:
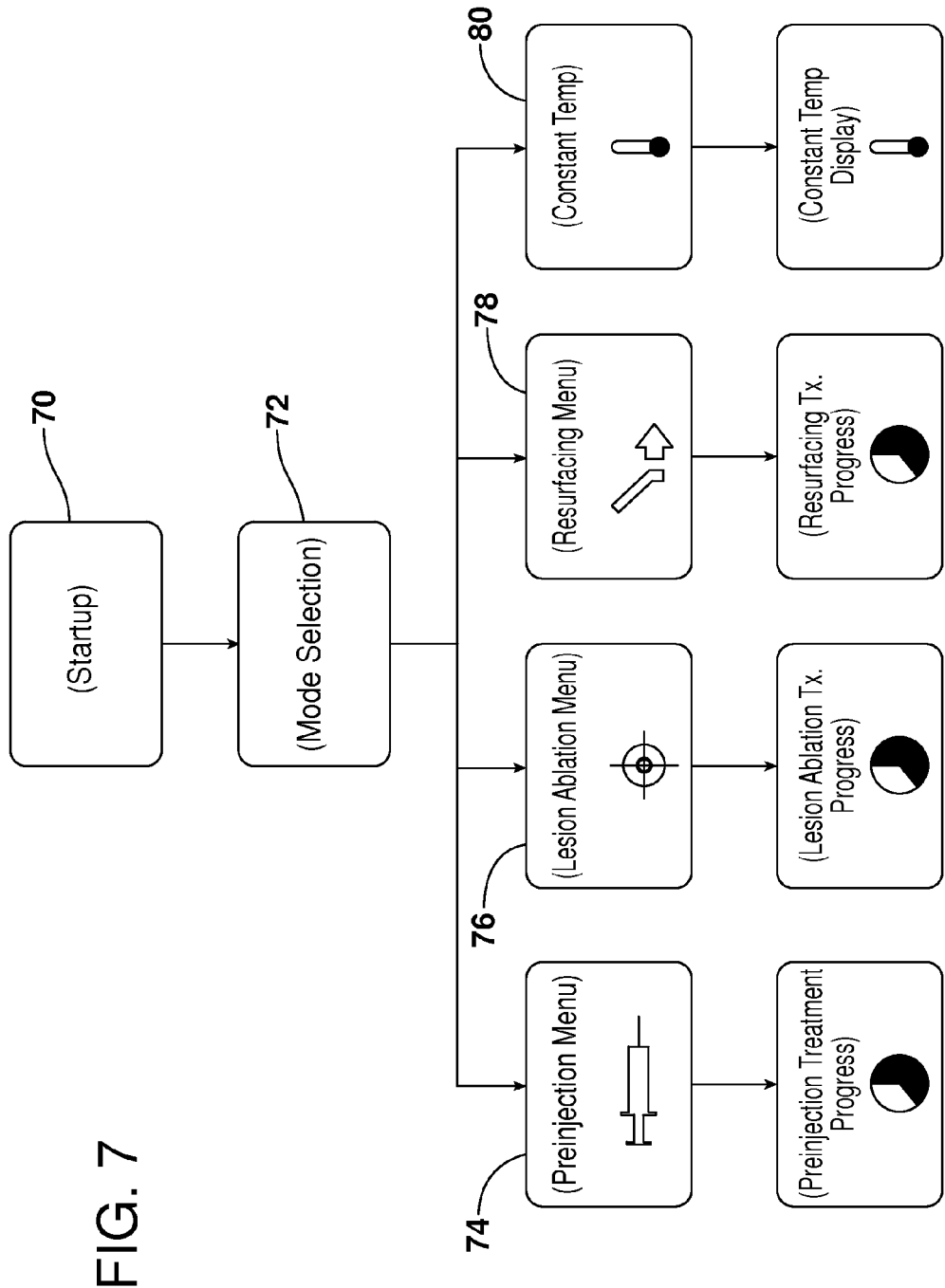
FIG. 7 is a flow chart of a menu hierarchy.

A flow chart of a menu hierarchy seen by the user on the display 64 is illustrated in FIG. 7. Exemplary screens are shown including a Startup screen 70, a Select Mode screen 72, a Preinjection Menu screen 74, a Lesion Ablation Menu screen 76, a Resurfacing Menu screen 78, and a Constant Temp screen 80. Additional progress and display screens are also shown. Upon initiation of a cooling cycle, the display 64 switches from parameter selection screens to treatment progress display screens. Additional indication of cycle progress may be provided on a display supported by the housing 12.

Figure 8:
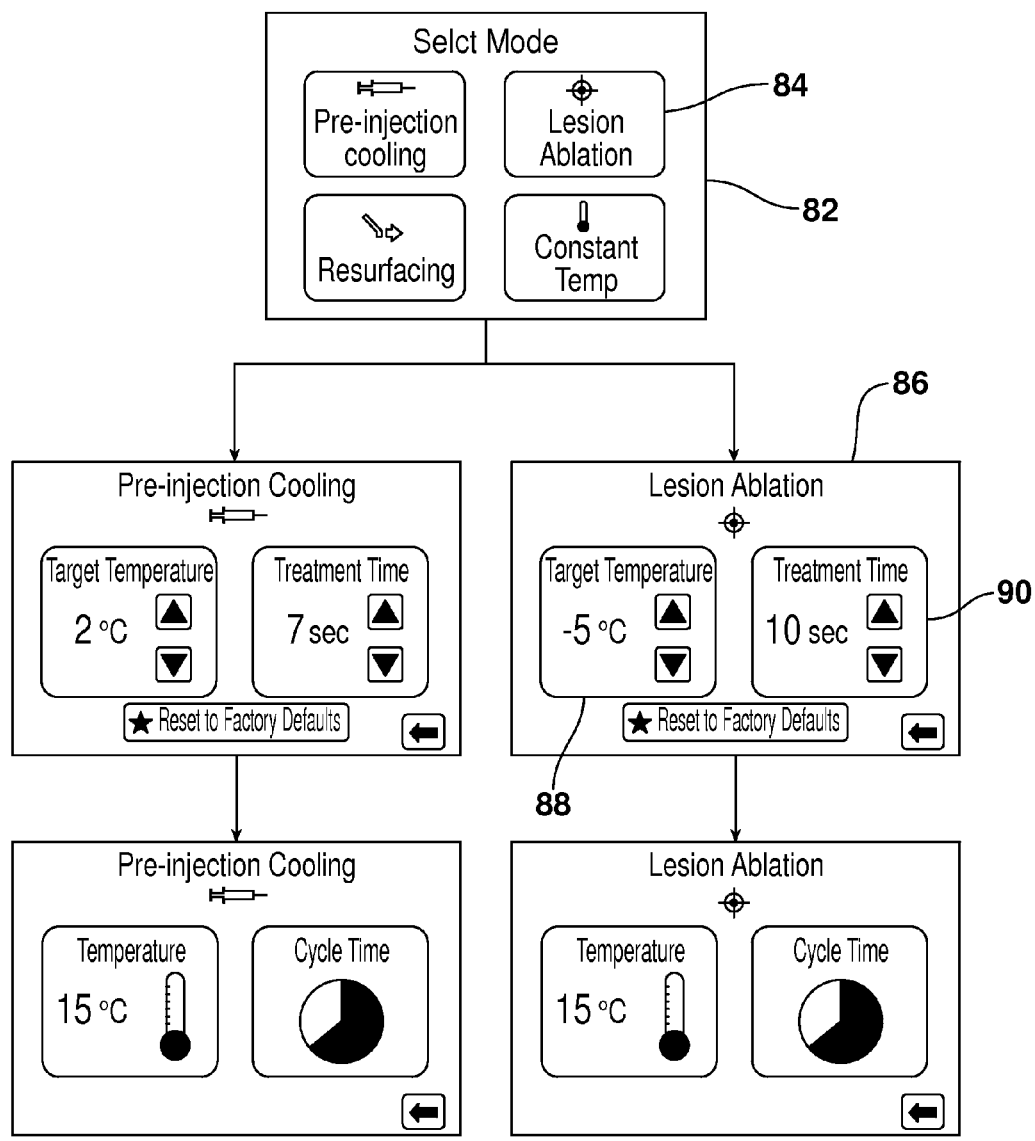
FIG. 8 is a detailed view of several of the display screens for the user interface at the touch screen display.

Additional screens are shown in FIG. 8 including an alternate Select Mode screen 82 and sub-display screens for each mode. The Select Mode screen 82, for example, is shown with four selection buttons (e.g., Lesion Ablation 84) representing four modes of operation of the device 10. Selecting the Lesion Ablation screen 84 opens a Lesion Ablation screen 86 which reveals a Target Temperature indicator and selector buttons 88, a Treatment Time indicator and selector buttons 90, and a reset button 92. It is clear that these screens and the displayed selectable operational parameters and settings can be varied in any manner dependent upon anything from procedure type to personal preference. All such variations are within the scope of the present invention.

Figure 9:
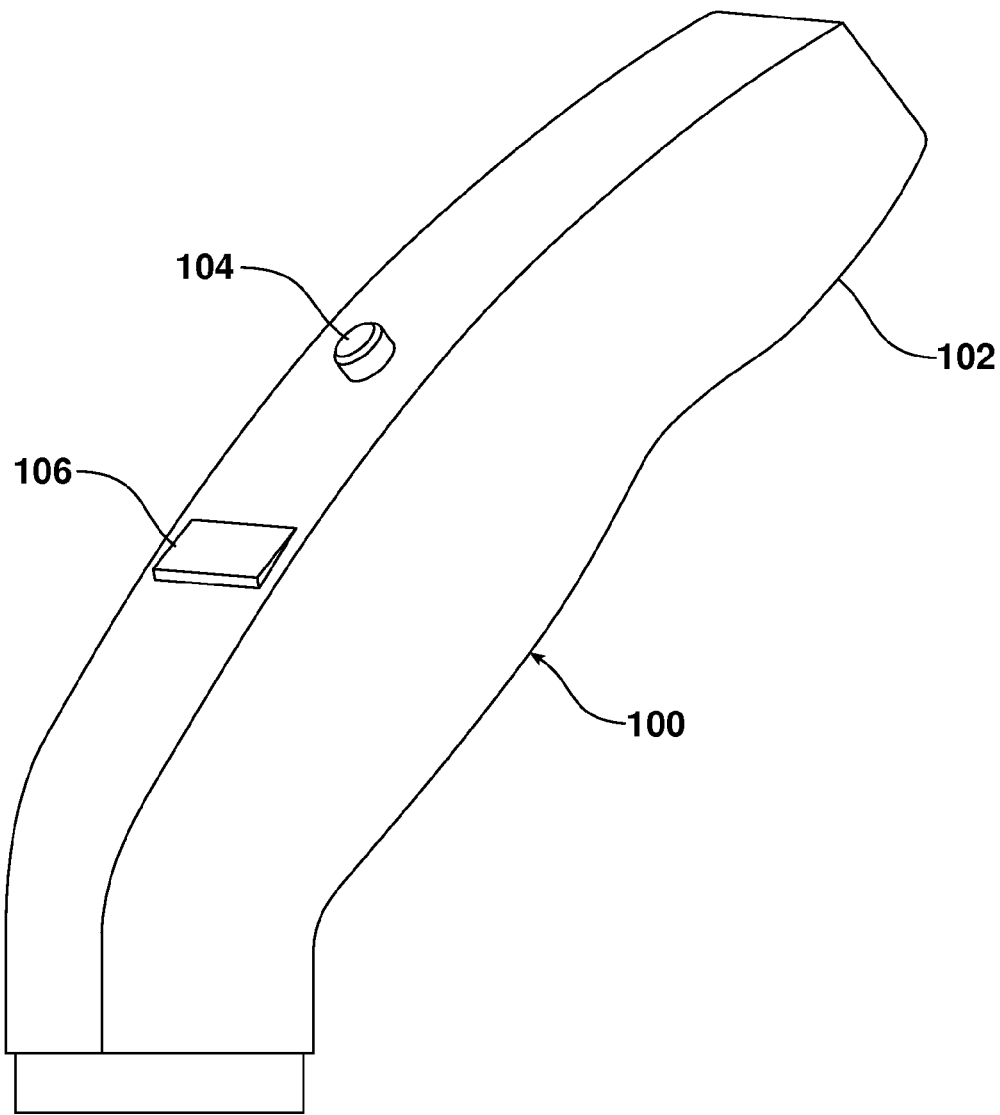
FIG. 9 is a perspective view of an alternate embodiment handpiece of a skin treatment device.

In an embodiment shown in FIG. 9, an alternate housing 100 for use with the device 10 and base unit 12 described above for effecting change in tissue at a treatment site by cooling the tissue at the treatment site is shown. In this embodiment, the housing 100 is shaped to be held in a user's hand during operation. More specifically, an outer shell 102 of the housing 100 is ergonomically designed both for operator and patient comfort and the overall size of the housing is kept small to allow access to the complex and small contours in the treatment area including those of the human face.

Figure 10:
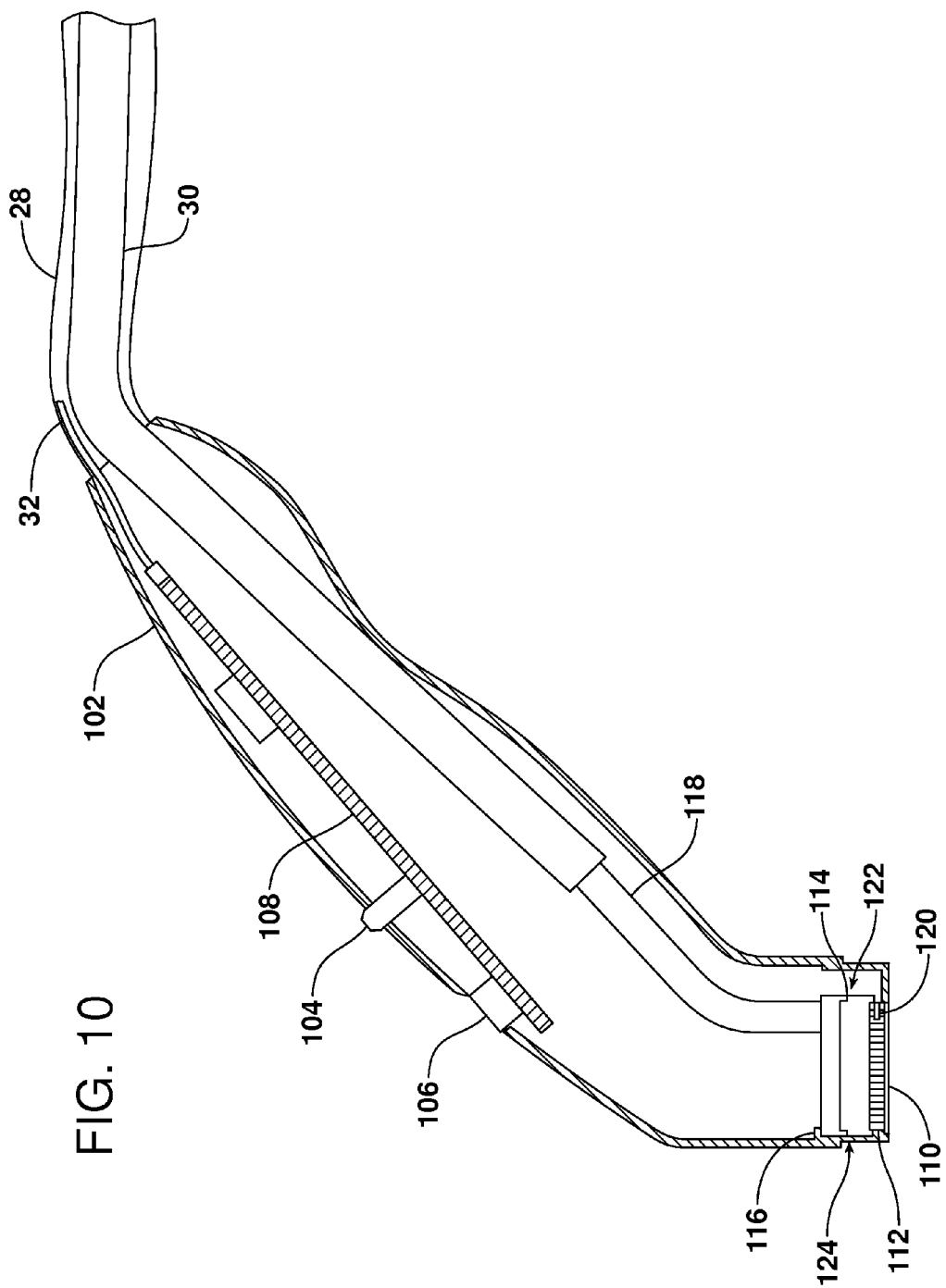
FIG. 10 is a section view of FIG. 9 showing a cold plate and TEC stack within the housing.

A switch 104 extends through the outer shell 102 of housing 100 for starting and stopping a cooling cycle, and a display 106 provides information to the user. For example, the display may alert the user of a time status of a cooling cycle, a temperature at the treatment site, cooling cycle completion, or other operational parameters and settings. As shown in FIG. 10, both the switch 104 and display 106 are mounted on a printed circuit board 108 supported within the housing 100. The printed circuit board 108 is electrically connected to the controller 54 through the electrical line 32 of cable 28.

A cold plate 110 is thermally coupled to a thermoelectric cooling semiconductor 112 within the housing 100. As described above, the thermoelectric cooling semiconductor 112 is a stacked array of thermoelectric cooling semiconductors or an TEC stack. In alternate embodiments, the TEC stack could include larger and/or additional thermoelectric cooling semiconductors which would provide a lower temperature at the treatment site. Such alternatives are dependent in some embodiments on the size of the housing. The TEC stack 112 is also electrically coupled to the power source 40 through electrical line 32 of cable 28. The power source 40 is positioned within base unit 14 in the present embodiment but could be positioned within the housing 100 in alternate embodiments.

The TEC stack 112 is also thermally coupled to a heat sink 114 to support thermal transfer, i.e., to remove heat generated by operation of the TEC stack. The heat sink 114 in the present embodiment is a water block having first and second portions as described above. Other types of heat sinks may be used to dissipate heat as is known in the art. As before, fluid is circulated to the heat sink 114 to transfer heat away from a hot side of TEC stack 112. Altogether, the cold plate 110, TEC stack 112, and heat sink 114 are held together in the present embodiment using a mechanical fastener (e.g., a screw). Abutments 116 are integrally molded within the housing 100 and stabilize the TEC stack 112, cold plate 110, and heat sink 114. The fluid is pumped from the base unit 14 through the fluid line 30 to housing 100. A rigid fluid tubing 118 connects the heat sink 114 and the fluid line 30. In the present embodiment, the fluid line 30 is flexible and routed within cable 28 away from the treatment site.

The device for effecting change in tissue at a treatment site of the embodiment shown in FIGS. 9 and 10 also includes a sensor 120 for sensing a temperature at the treatment site. More specifically, the sensor 120 senses a temperature of the cold plate 110 throughout operation and generates a signal ($S_{TEMP}$) indicative of the sensed temperature. The temperature of the cold plate 110 is synonymous with the temperature at the treatment site, and is maintained by the controller 54 as described above with regard to the change in tissue as a tissue function change or ablation of the tissue.

In the present embodiment, sensor 120 is embedded in or located adjacent to and in contact with the cold plate 110. Alternatively, the sensor 120 may be embedded between the cold plate 110 and the TEC stack 112. A recess 122 provides passage of wires (not shown) connecting the sensor 120 to the controller 54, as well as wires connecting the TEC stack 112 to the power source 40. As indicated above, the sensor 112 may be an infrared thermometer and a window (not shown) may be positioned adjacent the treatment site through which the infrared thermometer visualizes the tissue.

Figure 11:
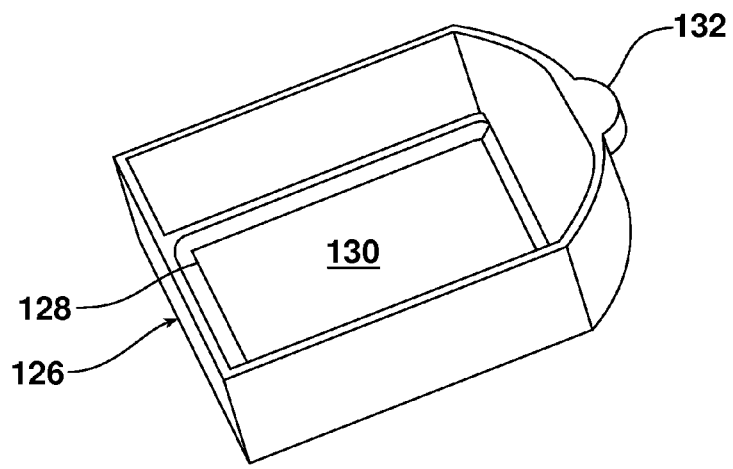
FIG. 11 is a perspective view of a full aperture disposable sheath.

In order to maintain cleanliness of a treatment end of the housing 100, a recess 124 is formed in housing 100 in this embodiment for attachment of a disposable sheath 126. The sheath 126, shown in FIG. 11, is attached to the housing 100 to prevent direct contact between the cold plate/device and the treatment site. In the present embodiment, the sheath 126 is snapped onto the housing 100 by means of a snap-on/snap-off mechanism and an optional thermally conductive medium, such as a liquid or gel, may be used between the sheath 126 and the treatment site.

The sheath 126 includes an aperture 128 and a thin film 130 covering the aperture. The thin film 130 is made of polypropylene, or other thin film, which does not necessarily have to be a good thermal conductor so long as the material is of minimal thickness. In this embodiment, the aperture 128 is sufficiently large to allow the treatment site to be exposed to essentially the full size of the cold plate 110. A flange 132 is provided on one edge of the sheath 126 to facilitate removal.

Figure 12A:
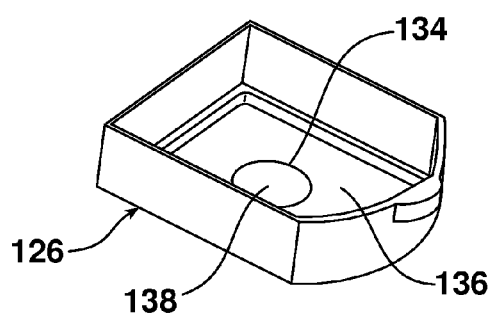
FIG. 12A is a perspective view of a reduced aperture disposable sheath.
Figure 12B:
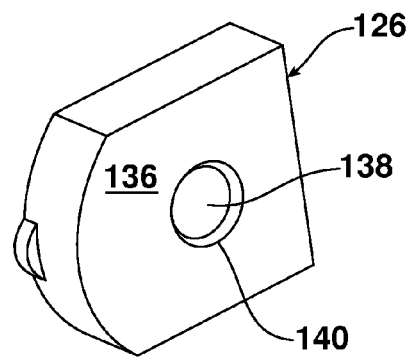
FIG. 12B is a perspective view of the reduced aperture disposable sheath showing chamfers around the reduced aperture.

In another embodiment shown in FIG. 12A, the disposable sheath 126 includes an aperture 134 of a reduced size for smaller treatment sites (e.g., for treating smaller lesions). In this manner, a portion of the cold plate 110 is occluded from the treatment site by a thicker shield 136. The aperture 134 is covered by a thin film 138. It should be noted that edges 140 of the sheath 126 may be chamfered, as shown in FIG. 12B, to facilitate contact with the treatment site.

In still other embodiments, air cooling is used to sink heat from the thermoelectric cooling semiconductor. Specifically, cooling fins are thermally coupled to the thermoelectric cooling semiconductor and cooled by a fan that forces or pulls air through the housing and over the cooling fins. Heated exhaust air may exit through a matched or single set of vent apertures. In this embodiment, a base unit for supplying electrical power and control signals may be used, or the device could be battery operated and entirely self-contained with control provided in the housing.

Another embodiment uses a heat sink contained in the housing made from a high heat capacity material. The device which is essentially a housing including the thermoelectric cooling semiconductor and control circuits is battery powered allowing the device to operate without a tether to a base unit, and to consume minimal power by avoiding utilization of a cooling fan. This embodiment is intended to operate until the battery is exhausted or the heat sink material reaches a maximum temperature.

In accordance with another aspect of the invention, a method of effecting change in tissue at a treatment site is provided. The method includes the steps of positioning a cold plate in thermal contact with the tissue at the treatment site, cooling the cold plate to a temperature sufficient to effect change in the tissue at the treatment site, sensing a temperature at the treatment site and generating a signal indicative of the temperature, and controlling the cooling of the cold plate dependent upon the sensed temperature.

In operation, a user positions a surface 24 of a cold plate 22 onto a desired location of a patient's skin at a treatment site. The cold plate 22 is cooled to a temperature sufficient to effect change in the tissue at the treatment site. The cooling step may occur prior to positioning the surface 24 of the cold plate 22 onto the treatment site or after the cold plate surface 24 is positioned. Cooling of the cold plate 22 is initiated in response to user input. In the present embodiment, the user input is provided through a switch which is a foot switch. Other means of initiating the cooling step may include, for example, a momentary switch mounted on a housing or a base unit, voice activation, or a sensor may detect an increase in temperature at the treatment site upon contact between the cold plate surface 24 and the patient's skin at the treatment site.

In response to the user input, a controller 54 in the form of a microprocessor energizes to the TEC stack 38, for example, which is thermally coupled to the cold plate 22 for cooling the surface 24 of the cold plate to a predetermined temperature sufficient to effect change in the tissue at the treatment site. A temperature sensor 48 is used to sense a temperature at the treatment site and generate a signal ($S_{TEMP}$) indicative of the temperature which is fed to the controller 54. The controller 54 can be configured to control all parameters of the cooling step dependent upon the sensed temperature. These parameters may include desired temperature, rate of cooling, and/or cycle time, among other parameters. In the present embodiment, temperature readings from the temperature sensor 48 at the treatment site are sent to the controller 54 according to a specified sampling time. Data tracking of each cycle is also possible with output to a display, internal storage, or another, possibly remote, computer.

In one embodiment, the cooling step includes maintaining the temperature sufficient to effect change in the tissue at the treatment site between approximately −1° C. and −40° C. When the change in tissue is a tissue function change, for example, the temperature sufficient to effect the tissue function change at the treatment site may be maintained by the controller 54 at approximately −1° C. When the change in tissue is ablation of the tissue, for example, the temperature sufficient to ablate the tissue at the treatment site may be maintained by the controller 54 at or below approximately −40° C. In operation, the operator may control the temperature to any degree desired but the approximately −1° C. temperature has been determined to be sufficient to effect tissue function change at the treatment site and the approximately −40° C. temperature has been determined to be sufficient to ablate tissue at the treatment site.

In another embodiment, the cooling step includes maintaining the temperature sufficient to effect change in the tissue at the treatment site for a period of time. In yet another, the timing cycle could be initiated when a certain minimum temperature is reached. In the present embodiment, the microprocessor 54 performs a real time calculation of the area under the temperature versus time curve. A 1/Temperature mathematical transformation is utilized so that as the temperature goes progressively lower, the area under the curve increases.

With any of these methods, the microprocessor 54 terminates the cycle when the desired parameters have been achieved. The user will be alerted to the completion of the cycle with a visual and/or audio signal and will subsequently remove the surface 24 of cold plate 22 from contact with the treatment site. The user can then move the surface 24 of cold plate 22 to a new treatment site. Note that the surface 24 of cold plate 22 will now be at a lower starting temperature and thus, the cooling cycle will be shorter. Likewise, if the next treatment site is near the previous treatment site, the skin at the new treatment site may also be at a lower temperature. By utilizing the data supplied by the temperature sensor 48, the controller 54 can adjust accordingly to provide an identical time versus temperature exposure time.

Depending on the desired clinical effect, standardized parameters can be utilized and stored in user modifiable or fixed presets. For example, a first preset could provide only enough cooling for a superficial resurfacing and a second preset could provide enough cooling for tissue ablation of a lesion. In an alternate embodiment, additional presets could be added for different uses, for example, for large area resurfacing. Even more, the controller 54 could be programmed to hold the surface 24 of the cold plate 22 at a constant temperature using the temperature sensor 48 for feedback. This would allow placement of the surface 24 of cold plate 22 on the patient's skin to initiate the cooling cycle.

In the present embodiment, the positioning step includes inserting at least one finger into an aperture 16 of a housing 12 supporting the cold plate 22. As noted above, the aperture 16 is a longitudinal bore within which the user's finger is positioned during use to support the housing 12. The longitudinal bore 16 could be wider in different embodiments for receiving more than one of the user's fingers. The housing 12 also includes two exterior surfaces 18, 20 for contacting second and third fingers of the user to stabilize the housing 12 during use.

More specifically, the user's finger ($F_1$) is inserted into the longitudinal bore 16 of housing 12. As shown in FIG. 2, the user's palm (P) is facing upwards and the second and third fingers ($F_2$, $F_3$) are juxtaposed to the longitudinal bore 16 and positioned on opposing sides of the housing 12. Upper and side surfaces of the second and third fingers are in contact with the exterior surfaces 18, 20 of the housing 12. In other words, the second and third fingers are positioned within the open channels formed by the exterior surfaces 18, 20 on opposing sides of the longitudinal bore 16. In this manner, the user can support the housing 12 with the finger $F_1$ and provide stabilization during use with the fingers $F_2$ and $F_3$.

Even more specifically, the user can apply a downward force to the housing 12 using finger $F_1$ and at the same time apply upward or stabilizing forces using fingers $F_2$ and $F_3$ This provides the user with a certain level of control and stability of the housing 12.

In still another embodiment, a method of effecting change in tissue at a treatment site is provided. This method includes the steps of positioning a cold plate in thermal contact with tissue at the treatment site, energizing at least one thermoelectric cooling semiconductor thermally coupled to the cold plate for gradually cooling the cold plate to a predetermined temperature sufficient to effect change in the tissue at the treatment site, sensing a temperature at the treatment site; and adjusting the energy applied to the at least one thermoelectric cooling semiconductor in order to maintain the temperature of the treatment site at a desired temperature. The method may further include the step of removing the energy applied to the at least one thermoelectric cooling semiconductor at the end of a period of time. Likewise, the adjusting step may be repeated for a predetermined period of time and the emerging step may be ended at the end of the predetermined period of time. As in the above method, the adjusting step depends on a sensed temperature at the treatment site.

In operation, a user positions a surface 24 of a cold plate 22 in thermal contact with a patient's skin at a treatment site. The cold plate 22 is cooled by energizing at least one thermoelectric cooling semiconductor 38 thermally coupled to the cold plate 22 for gradually cooling the cold plate to a predetermined temperature sufficient to effect change in the tissue at the treatment site. The energizing step may occur prior to positioning the surface 24 of the cold plate 22 onto the treatment site or after the cold plate surface 24 is positioned. Cooling of the cold plate 22 is initiated in response to user input as broadly described above.

In response to the user input, a controller 54 in the form of a microprocessor energizes the at least one thermoelectric cooling semiconductor (e.g., a TEC stack) 38 which is thermally coupled to the cold plate 22 for cooling the surface 24 of the cold plate to the predetermined temperature sufficient to effect change in the tissue at the treatment site. A temperature sensor 48 is used to sense a temperature at the treatment site and generate a signal ($S_{TEMP}$) indicative of the temperature which is fed to the controller 54. As described above, the controller 54 can be configured to control all parameters of the cooling step dependent upon the sensed temperature.

In one embodiment, the temperature sufficient to effect change in the tissue at the treatment site is maintained for a period of time after which the energy is removed from the TEC stack 38. In another embodiment, the microprocessor 54 terminates the cycle when the desired parameters have been achieved. In other words, the step of adjusting the energy applied to the TEC stack 38 is repeated for a predetermined period of time. At the end of this period, the energizing step is ended.

Even more, the positioning step of the present method includes inserting at least one finger into an aperture 16 of a housing 12 supporting the cold plate 22 and stabilizing the cold plate in thermal contact with tissue at the treatment site by positioning second and third fingers ($F_2$, $F_3$) in juxtaposition to the longitudinal bore 16 on opposing sides of the housing 12. Upper and side surfaces of the second and third fingers are in contact with the exterior surfaces 18, 20 of the housing 12. In other words, the second and third fingers are positioned within the open channels formed by the exterior surfaces 18, 20 on opposing sides of the longitudinal bore 16. In this manner, the user can support the housing 12 with the finger $F_1$ and provide stabilization during use with the fingers $F_2$ and $F_3$.

The foregoing description of the present and alternate embodiments of the invention has been presented for purposes of illustration and description. It is not intended to be exhaustive or to limit the invention to the precise forms disclosed. Obvious modifications or variations are possible in light of the above teachings. The present and alternate embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

The invention claimed is:

1. A device for effecting change in tissue at a treatment site comprising:
   a housing having an aperture for receiving a user's finger;
   a cold plate supported by said housing for cooling the tissue at the treatment site; and
   at least one thermoelectric cooling semiconductor thermally coupled to said cold plate and electrically coupled to a power source, wherein the aperture for receiving the user's finger is a longitudinal bore, and said housing includes at least one exterior surface for contacting a second finger of the user to stabilize the device during use.

2. The device for effecting change in tissue at a treatment site of claim 1, wherein said cold plate includes a surface for contacting the treatment site, and at least a portion of said cold plate including said surface extends from a housing supporting said cold plate.

3. The device for effecting change in tissue at a treatment site of claim 1, wherein said housing includes a first surface for contacting the second finger of the user and a second surface for contacting a third finger of the user.

4. The device for effecting change in tissue at a treatment site of claim 3, wherein said first and second surfaces are on opposing sides of the aperture for receiving the user's finger.

5. The device for effecting change in tissue at a treatment site of claim 4, wherein said first and second surfaces form open channels.

6. The device for effecting change in tissue at a treatment site of claim 1, wherein said housing includes first and second surfaces juxtaposed to and on opposing sides of the aperture for contacting the user during use.

7. A device for effecting change in tissue at a treatment site comprising:
   a housing having an aperture for receiving a user's finger;
   a cold plate supported by said housing for cooling the tissue at the treatment site;
   at least one thermoelectric cooling semiconductor thermally coupled to said cold plate and electrically coupled to a power source;
   a heat sink thermally coupled to said at least one thermoelectric cooling semiconductor;
   a sensor for sensing a temperature at the treatment site; and
   a controller electrically coupled to said power source, said controller for controlling the temperature at the treatment site dependent upon the sensed temperature at the treatment site, wherein the temperature at the treatment site is a temperature of said cold plate.

8. The device for effecting change in tissue at a treatment site of claim 7, wherein said cold plate includes a surface for contacting the treatment site, and at least a portion of said cold plate including said surface extends from said housing.

9. The device for effecting change in tissue at a treatment site of claim 7, wherein the aperture is a longitudinal bore and first and second surfaces of said housing form open channels for contacting second and third fingers to secure the device during use.

10. The device for effecting change in tissue at a treatment site of claim 7, wherein said controller controls the temperature at the treatment site dependent upon the sensed temperature at the treatment site and a target temperature.

11. The device for effecting change in tissue at a treatment site of claim 10, wherein the sensor is an infrared thermometer.

12. The device for effecting change in tissue at a treatment site of claim 7, wherein said housing includes a first surface for contacting a second finger of the user and a second surface for contacting a third finger of the user, and wherein said first and second surfaces are on opposing sides of the aperture for receiving the user's finger.

13. The device for effecting change in tissue at a treatment site of claim 7, wherein the aperture is a longitudinal bore.

14. A device for effecting change in tissue at a treatment site comprising:
   a power source;
   a cold plate for cooling the tissue at the treatment site;
   at least one thermoelectric cooling semiconductor thermally coupled to said cold plate and electrically coupled to said power source;
   a heat sink thermally coupled to said at least one thermoelectric cooling semiconductor;
   a sensor for sensing a temperature at the treatment site; and
   a controller electrically coupled to said power source, said controller for controlling the temperature at the treatment site dependent upon the sensed temperature at the treatment site, wherein the change in the tissue is a tissue function change and the temperature sufficient to effect the tissue function change at the treatment site is maintained by said controller at approximately −1° C.

15. The device for effecting change in tissue at a treatment site of claim 14, wherein said cold plate includes a surface for contacting the treatment site, and at least a portion of said cold plate including said surface extends from a housing supporting said cold plate.

16. The device for effecting change in tissue at a treatment site of claim 14, further comprising a housing having an aperture for receiving a user's finger.

17. The device for effecting change in tissue at a treatment site of claim 16, wherein the aperture for receiving the user's finger is a longitudinal bore, and said housing includes at least one exterior surface for contacting a second finger of the user to stabilize the device during use.

18. A device for effecting change in tissue at a treatment site comprising:
   a power source;
   a cold plate for cooling the tissue at the treatment site;
   at least one thermoelectric cooling semiconductor thermally coupled to said cold plate and electrically coupled to said power source;
   a heat sink thermally coupled to said at least one thermoelectric cooling semiconductor;
   a sensor for sensing a temperature at the treatment site;
   a controller electrically coupled to said power source, said controller for controlling the temperature of the treatment site dependent upon the sensed temperature of the treatment site; and
   a housing having an aperture for receiving a user's finger.

19. The device for effecting change in tissue at a treatment site of claim 18, wherein the aperture for receiving the user's finger is a longitudinal bore, and said housing includes at least one exterior surface for contacting a second finger of the user to stabilize the device during use.

20. The device for effecting change in tissue at a treatment site of claim 18, further comprising a housing having an aperture for receiving a user's finger.

21. The device for effecting change in tissue at a treatment site of claim 20, wherein the aperture for receiving the user's finger is a longitudinal bore, and said housing includes at least one exterior surface for contacting a second finger of the user to stabilize the device during use.

22. A device for effecting change in tissue at a treatment site comprising:
   a power source;
   a cold plate for cooling the tissue at the treatment site;
   at least one thermoelectric cooling semiconductor thermally coupled to said cold plate and electrically coupled to said power source;
   a heat sink thermally coupled to said at least one thermoelectric cooling semiconductor;
   a sensor for sensing a temperature at the treatment site;
   a controller electrically coupled to said power source, said controller for controlling the temperature of the treatment site dependent upon the sensed temperature of the treatment site, wherein the change in the tissue is ablation of the tissue and the temperature sufficient to ablate the tissue at the treatment site is maintained by said controller at or below approximately −40° C.

23. The device for effecting change in tissue at a treatment site of claim 22, further comprising a housing having an aperture for receiving a user's finger.

24. The device for effecting change in tissue at a treatment site of claim 23, wherein the aperture for receiving the user's finger is a longitudinal bore, and said housing includes at least one exterior surface for contacting a second finger of the user to stabilize the device during use.

25. The device for effecting change in tissue at a treatment site of claim 22, further comprising a housing having an aperture for receiving a user's finger.

26. The device for effecting change in tissue at a treatment site of claim 25, wherein the aperture for receiving the user's finger is a longitudinal bore, and said housing includes at least one exterior surface for contacting a second finger of the user to stabilize the device during use.

27. A method of effecting change in tissue at a treatment site comprising the steps of:
   positioning a cold plate in thermal contact with tissue at the treatment site;
   cooling said cold plate to a temperature sufficient to effect change in the tissue at the treatment site;
   sensing a temperature at the treatment site and generating a signal indicative of the temperature; and
   controlling the cooling of said cold plate dependent upon the sensed temperature, wherein the controlling step includes maintaining the temperature sufficient to effect change in the tissue at the treatment site between approximately −1° C. and −40° C.

28. The method of effecting change in tissue at a treatment site of claim 27, wherein the controlling step includes maintaining the temperature sufficient to effect change in the tissue at the treatment site for a period of time.

29. The method of effecting change in tissue at a treatment site of claim 27, wherein the step of maintaining the temperature sufficient to effect change in the tissue at the treatment site includes the step of ending the cooling at the end of the predetermined period of time.

30. A method of effecting change in tissue at a treatment site comprising the steps of:
   positioning a cold plate in thermal contact with tissue at the treatment site;
   cooling said cold plate to a temperature sufficient to effect change in the tissue at the treatment site;
   sensing a temperature at the treatment site and generating a signal indicative of the temperature; and
   controlling the cooling of said cold plate dependent upon the sensed temperature, wherein the positioning step includes inserting at least one finger into an aperture of a housing supporting said cold plate.

31. The method of effecting change in tissue at a treatment site of claim 30, wherein the controlling step includes maintaining the temperature sufficient to effect change in the tissue at the treatment site.

32. The method of effecting change in tissue at a treatment site of claim 31, wherein the step of maintaining the temperature sufficient to effect change in the tissue at the treatment site is repeated for a predetermined period of time.

33. The method of effecting change in tissue at a treatment site of claim 30, wherein the temperature sufficient to effect change is between approximately −1° C. and −40° C.

34. A method of effecting change in tissue at a treatment site comprising the steps of:
   positioning a cold plate in thermal contact with tissue at the treatment site;
   cooling said cold plate to a temperature sufficient to effect change in the tissue at the treatment site;
   sensing a temperature at the treatment site and generating a signal indicative of the temperature;
   controlling the cooling of said cold plate dependent upon the sensed temperature; and stabilizing said cold plate in thermal contact with tissue at the treatment site.

35. The method of effecting change in tissue at a treatment site of claim 34, wherein the stabilizing step includes inserting at least one finger into an aperture of a housing supporting said cold plate.

36. The method of effecting change in tissue at a treatment site of claim 34, wherein the controlling step includes maintaining the temperature sufficient to effect change in the tissue at the treatment site.

37. The method of effecting change in tissue at a treatment site of claim 36, wherein the temperature sufficient to effect change is between approximately −1° C. and −40° C.

* * * * *